United States Patent
Kim

(10) Patent No.: US 9,907,837 B2
(45) Date of Patent: *Mar. 6, 2018

(54) COMPOSITION FOR PREVENTING OR TREATING CACHEXIA

(71) Applicants: GemVax & KAEL Co., Ltd., Daejeon (KR); Sang Jae Kim, Seoul (KR)

(72) Inventor: Sang Jae Kim, Seoul (KR)

(73) Assignee: GemVax & KAEL Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/400,299

(22) PCT Filed: May 10, 2013

(86) PCT No.: PCT/KR2013/004176
§ 371 (c)(1),
(2) Date: Aug. 26, 2015

(87) PCT Pub. No.: WO2013/169077
PCT Pub. Date: Nov. 14, 2013

(65) Prior Publication Data
US 2015/0353903 A1 Dec. 10, 2015

(30) Foreign Application Priority Data

May 11, 2012 (KR) .................. 10-2012-0050529
May 11, 2012 (KR) .................. 10-2012-0050533
Jul. 2, 2012 (KR) .................. 10-2012-0071989
Sep. 19, 2012 (KR) .................. 10-2012-0104207

(51) Int. Cl.
| | |
|---|---|
| *C12N 9/12* | (2006.01) |
| *A23L 1/305* | (2006.01) |
| *A61K 38/45* | (2006.01) |
| *A61K 38/10* | (2006.01) |
| *A61K 9/00* | (2006.01) |
| *A23L 33/18* | (2016.01) |
| *A61K 38/00* | (2006.01) |

(52) U.S. Cl.
CPC .............. *A61K 38/45* (2013.01); *A23L 33/18* (2016.08); *A61K 9/0019* (2013.01); *A61K 38/10* (2013.01); *C12N 9/1276* (2013.01); *A23V 2002/00* (2013.01); *A61K 38/00* (2013.01); *C12Y 207/07049* (2013.01)

(58) Field of Classification Search
None
See application file for complete search history.

(56) References Cited

U.S. PATENT DOCUMENTS

| | | |
|---|---|---|
| 6,967,211 B2 | 11/2005 | Inoue |
| 7,030,211 B1 | 4/2006 | Gaudernack et al. |
| 7,794,723 B2 | 9/2010 | Gaudernack et al. |
| 8,828,403 B2 | 9/2014 | Filaci et al. |
| 8,933,197 B2 | 1/2015 | Stemmer et al. |
| 9,023,987 B2 | 5/2015 | Chung et al. |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1* | 5/2006 | Gaudernack .......... A61K 38/45 530/326 |
| 2007/0190561 A1 | 8/2007 | Morin et al. |
| 2009/0136917 A1 | 5/2009 | Szalay et al. |
| 2009/0186802 A1 | 7/2009 | Alluis et al. |
| 2009/0215852 A1* | 8/2009 | Bascomb ............. A61K 31/138 514/411 |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0065124 A1 | 3/2012 | Morishita et al. |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim |
| 2015/0307859 A1 | 10/2015 | Kim |
| 2015/0343095 A1 | 12/2015 | Kim |
| 2016/0002613 A1 | 1/2016 | Kim |

(Continued)

FOREIGN PATENT DOCUMENTS

| | | |
|---|---|---|
| EP | 1020190 A3 | 10/2000 |
| EP | 1093381 B2 | 7/2009 |

(Continued)

OTHER PUBLICATIONS

Tisdale ("Mechanisms of Cancer Cachexia"; Physiol. Rev 80:381-410, 2009).*
Tisdale ("Catabolic mediators of cancer cachexia" Curr. Opin Support Pallat Care,Dec. 2008: 2(4):256-61).*
Beer, T.M., et al., "Phase II Study of Weekly Docetaxel in Symptomatic Androgen-independent Prostate Cancer," Annals of Oncology 12(9):1273-1279, Oxford University Press, England (2001).
Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).

(Continued)

*Primary Examiner* — James H Alstrum-Acevedo
*Assistant Examiner* — Tara L Martinez
(74) *Attorney, Agent, or Firm* — Sterne, Kessler, Goldstein & Fox P.L.L.C.

(57) ABSTRACT

The present invention relates to composition for preventing or treating cachexia, and more specifically, to a composition for preventing or treating cachexia containing a peptide derived from a telomerase. The composition for preventing or treating cachexia, according to present invention, has the advantages of improving symptoms of cachexia, such as weight loss, anemia, edema, and loss of appetite, and has few side effects.

16 Claims, 5 Drawing Sheets

(56) References Cited

U.S. PATENT DOCUMENTS

| | | | |
|---|---|---|---|
| 2016/0008438 A1 | 1/2016 | Kim | |
| 2016/0082089 A1 | 3/2016 | Kim | |
| 2016/0120966 A1 | 5/2016 | Kim | |
| 2016/0137695 A1 | 5/2016 | Kim | |
| 2016/0151512 A1 | 6/2016 | Kim | |
| 2016/0250279 A1 | 9/2016 | Kim | |
| 2016/0296604 A1 | 10/2016 | Kim | |
| 2016/0375091 A1 | 12/2016 | Kim | |

FOREIGN PATENT DOCUMENTS

| | | |
|---|---|---|
| EP | 1817337 B1 | 1/2011 |
| JP | 2010252810 A | 11/2010 |
| JP | 5577472 B2 | 8/2014 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120087885 A | 8/2012 |
| KR | 20120121196 A | 11/2012 |
| KR | 20120130996 A | 12/2012 |
| KR | 20120133661 A | 12/2012 |
| WO | WO-0002581 A1 | 1/2000 |
| WO | WO-2010003520 A2 | 1/2010 |
| WO | WO-2010012850 A1 | 2/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167574 A1 | 11/2013 |
| WO | WO-2013169060 A1 | 11/2013 |
| WO | WO-2013169067 A1 | 11/2013 |
| WO | WO-2014010971 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |

OTHER PUBLICATIONS

Bruns, A.F., et al., "A Heat-shock Protein Axis Regulates VEGFR2 Proteolysis, Blood Vessel Development and Repair," PloS One 7(11):e48539, Public Library of Science, United States (2012).
Calderwood, S.K., et al., "Heat Shock Proteins in Cancer: Chaperones of Tumorigenesis," Trends in Biochemical Sciences 31(3):164-172, Elsevier Trends Journals, England (2006).
Dempsey, N.C., et al., "Differential Heat Shock Protein Localization in Chronic Lymphocytic Leukemia," Journal of Leukocyte Biology 87(3):467-476, Society for Leukocyte Biology, United States (2010).

Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Ferrarini, M., et al., "Unusual Expression and Localization of Heat-shock Proteins in Human Tumor Cells," International Journal of Cancer 51(4):613-619, Wiley-Liss, United States (1992).
Garcia-Carbonero, R., et al., "Inhibition of HSP90 Molecular Chaperones: Moving Into the Clinic," The Lancet Oncology 14(9):e358-e369, Lancet Publishing Group, England (2013).
Henry, J.Y., et al., "Lenalidomide Enhances the Anti-prostate Cancer Activity of Docetaxel in vitro and in vivo," The Prostate 72(8):856-867, Wiley-Liss, United States (2012).
International Preliminary Report on Patentability for International Application No. PCT/KR2014/011280, The International Bureau of WIPO, Geneva, Switzerland, dated May 24, 2016, 15 pages.
International Search Report for International Application No. PCT/KR2014/011280, Korean Intellectual Property Office, Republic of Korea, dated Feb. 11, 2015, 12 pages.
International Search Report for International Application No. PCT/KR2014/012502, Korean Intellectual Property Office, Republic of Korea, dated Mar. 11, 2015, 10 pages.
International Preliminary Report on Patentability for International Application No. PCT/KR2014/012502, The International Bureau of WIPO, Geneva, Switzerland, dated Jun. 21, 2016, 22 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jemal, A., et al., "Cancer Statistics, 2008," CA: A Cancer Journal for Clinicians 58(2):71-96, Wiley, United States (2008).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).
Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).
Morano, K.A., "New Tricks for an Old Dog: the Evolving World of Hsp70," Annals of the New York Academy of Sciences 1113:1-14, Blackwell, United States (2007).
Murphy, M.E., "The Hsp70 Family and Cancer," Carcinogenesis 34(6):1181-1188, Irl Press, England (2013).
Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).

(56) References Cited

OTHER PUBLICATIONS

Seo, J.S., et al., "T Cell Lymphoma in Transgenic Mice Expressing the Human Hsp70 Gene," Biochemical and Biophysical Research Communications 218(2):582-587, Elsevier, United States (1996).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Uehara, Y., "Natural Product Origins of Hsp90 Inhibitors," Current Cancer Drug Targets 3(5):325-330, Bentham Science Publishers, Netherlands (2003).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Volloch, V.Z. and Sherman, M.Y., "Oncogenic Potential of Hsp72," Oncogene 18(24):3648-3651, Nature Publishing Group, England (1999).
Written Opinion for International Application No. PCT/KR2014/011280, Korean Intellectual Property Office, Republic of Korea, dated Feb. 11, 2015, 14 pages.
Written Opinion for International Application No. PCT/KR2014/012502, Korean Intellectual Property Office, Republic of Korea, dated Mar. 11, 2015, 20 pages.
Yeh, C.H., et al., "Clinical Correlation of Circulating Heat Shock Protein 70 in Acute Leukemia," Leukemia Research 34(5):605-609, Pergamon Press, England (2010).
Zhou, J., et al., "PI3K/Akt Is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Altschul, S.F., et al., "Basic Local Alignment Search Tool," Journal of Molecular Biology 215(3):403-410, Elsevier, England (1990).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Cho, Y.J., "GemVax & Kael (082270)," Hana Daetoo Securities, Company Report, Sep. 10, 2012, 8 pages.
Co-pending U.S. Appl. No. 14/413,732, inventor Sang Jae Kim, filed Jul. 11, 2013 (Not Published).
Co-pending U.S. Appl. No. 14/896,358, inventor Sang Jae Kim, filed Dec. 4, 2015 (Not Published).
Co-pending U.S. Appl. No. 14/899,746, inventor Sang Jae Kim, filed Apr. 12, 2015 (Not Published).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
Dinarello, C.A., "Interleukin-1 in the Pathogenesis and Treatment of Inflammatory Diseases," Blood 117(14):3720-3732, American Society of Hematology, United States (2011).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).

Fujii, H., et al., "Telomerase Insufficiency in Rheumatoid Arthritis," Proceedings of the National Academy of Sciences USA 106(11):4360-4365, National Academy of Sciences, United States (2009).
GemVax Receives Report on Anti-Inflammatory Mechanism, The Asia Economy Daily, Article written on May 7, 2013.
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Heitz, F., et al., "Twenty Years of Cell-Penetrating Peptides: From Molecular Mechanisms to Therapeutics," British Journal of Pharmacology 157(2):195-206, Wiley, England (2009).
HSE, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014,14 pages.
International Preliminary Report on Patentability for International Application No. PCT/KR2013/004176, The International Bureau of WIPO, Switzerland, dated Nov. 11, 2014,14pages.
International Preliminary Report on Patentability for International Application No. PCT/KR2013/006218, The International Bureau of WIPO, Switzerland, dated Jan. 13, 2015,27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.

(56) References Cited

OTHER PUBLICATIONS

International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Patent Application No. PCT/KR2013/004156, Korean Intellectual Property Office, Republic of Korea, dated Aug. 14, 2013, 10 pages.
International Search Report for International Application No. PCT/KR2013/008459, Korean Intellectual Property Office, Republic of Korea, dated Dec. 23, 2013, 8 pages.
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Myers, L.K., et al., "Collagen-Induced Arthritis, an Animal Model of Autoimmunity," Life Sciences 61(19):1861-1878, Elsevier, Netherlands (1997).
National Horizon Scanning Centre News on Emerging Technologies in Healthcare, GV1001 for Advanced and/or Metastatic Pancreatic Cancer, Published Apr. 2008.
NCBI, Reference Sequence: XP_003776612.1 (Jul. 17, 2012).
Novina, C.D. and Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences 98(18): 10308-10313, National Academy of Sciences, United States (2001).
Pearson, W.R. and Lipman, D.J., "Improved Tools for Biological Sequence Comparison," Proceedings of the National Academy of Sciences USA 85(8):2444-2448, National Academy of Sciences, United States (1988).
Rana, T.M., "Illuminating the Silence: Understanding the Structure and Function of Small RNAs," Nature Reviews. Molecular Cell Biology 8(1):23-36, Nature Publishing Group, England (2007).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).
Smith, T.F. and Waterman, M.S., "Comparison of Biosequences," Advances in Applied Mathematics 2(4):482-489, Academic Press, Inc., United States (1981).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).
Tomari Y. and Zamore, P.D., "Perspective: Machines for RNAi," Genes and Development 19(5):517-529, Cold Spring Harbor Laboratory Press, United States (2005).
Vennela, B., et al., "Current and Future Strategies for Therapy of Pancreatic Cancer," International Journal of Research in Pharmacy and Medicine 2(3):728-740 (2012).
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2013/008459, Korean Intellectual Property Office, Republic of Korea, dated Dec. 23, 2013, 9 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Shay, J.W., et al., "Telomerase therapeutics for cancer: challenges and new directions," Nature Reviews Drug Discovery 5(7): 577-584, Nature Publishing Group, England (2006).
Choi, S.G., "Recent Advances in Cancer Cachexia," Journal of Korean Oncology Nursing 11(1):20-25 (2011).
Engineer, D.R. and Garcia, J.M., "Leptin in Anorexia and Cachexia Syndrome," International Journal of Peptides 2012:Article ID 287457, Hindawi Publishing Corporation, United States (2012).
Ghaneh, P., et al., "Biology and Management of Pancreatic Cancer," Gut 56(8):1134-1152, British Medical Association, England (2007).
International Searching Authority, International Search Report for International Application No. PCT/KR2013/004176, Korean Intellectual Property Office, Republic of Korea, dated Aug. 6, 2013, 10 pages.
Kern, K.A. and Norton, J.A., "Cancer Cachexia," Journal of Parenteral and Enteral Nutrition 12(3):286-298, Sage Publications, United States (1988).
Kim, H.O. and Lee, S.I., "Experimental Animal Models for Rheumatoid Arthritis: Methods and Applications," Journal of Rheumatic Diseases 19(4):189-195 (2012).

(56) References Cited

OTHER PUBLICATIONS

Kyte, J.A., "Cancer Vaccination with Telomerase Peptide GV1001," Expert Opinion on Investigational Drugs 18(5):687-694, Taylor & Francis, England (2009).

Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).

Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).

Roubenoff, R., et al., "Adjuvant Arthritis as a Model of Inflammatory Cachexia," Arthritis and Rheumatism 40(3):534-539, Wiley-Blackwell, United States (1997).

Tisdale, M.J., "Mechanisms of Cancer Cachexia," Physiological Reviews 89(2):381-410, American Physiological Society, United States (2009).

Walsmith, J. and Roubenoff, R., "Cachexia in Rheumatoid Arthritis," International Journal of Cardiology 85(1):89-99, Elsevier, Netherlands (2002).

International Searching Authority, Written Opinion for International Application No. PCT/KR2013/004176, Korean Intellectual Property Office, Republic of Korea, dated Aug. 6, 2013, 7 pages.

Brandenburg, K., et al., "Peptide-based Treatment of Sepsis," Applied Microbiology and Biotechnology 90(3):799-808, Springer International, Germany (2011).

Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).

Stevenson, C.L., "Advances in Peptide Pharmaceuticals," Current Pharmaceutical Biotechnology 10(1):122-137, Bentham Science Publishers, Netherlands (2009).

Co-pending U.S. Appl. No. 14/400,293; inventor Sang Jae Kim; filed Sep. 9, 2015 (Not Published).

Dementia from Merck Manual, accessed on Jul. 29, 2009, pp. 1-17.

Mattson, M.P., "Pathways Towards and Away From Alzheimer's Disease," Nature 430(7000):631-639, Nature Publishing Group, England (2004).

McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).

Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).

Rheumatoid Arthritis from Merck Manual, accessed on Apr. 21, 2016, pp. 1-18.

Schenk, D., et al., "Immunization with Amyloid-beta Attenuates Alzheimer-disease-like Pathology in the PDAPP Mouse," Nature 400(6740):173-177, Nature Publishing Group, England (1999).

Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).

Sasada, A, et al. "A case of elderly patient with lung cancer efficiently treated with Dendritic Cell Immunotherapy," The 20th International Congress of Personalized Medicine, Conference Program and Abstracts, Personalized Medicine Universe (Japanese edition) 4(Supplement I): 2 pages, May 24, 2015.

"Seoul National University Bundang Hospital excited because of '000'," Clinical trials of Dream Anticancer Drug without side effects with Kael & GemVax, 4 pages, Apr. 22, 2013.

Eisenegger, C., et al., "The Role of Testosterone in Social Interaction," Trends in Cognitive Sciences 15(6):263-271, Elsevier Science, England (2011).

Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).

Guo, R.F., et al., "Regulatory Effects of Eotaxin on Acute Lung Inflammatory Injury," Journal of Immunology 166(8):5208-5218, American Association of Immunologists, United States (2001).

Morishita, M., and Peppas, N.A., "Is the Oral Route Possible for Peptide and Protein Drug Delivery?," Drug Discovery Today 11(19-20):905-910, Elsevier Science Ltd., England (2006).

National Institute of Diabetes and Digestive and Kidney Diseases, "Prostate Enlargement: Benign Prostatic Hyperplasia," Updated Sep. 2014, 14 pages.

Shaw, V.E., et al., "Current Status of GV1001 and Other Telomerase Vaccination Strategies in the Treatment of Cancer," Expert Review of Vaccines 9(9):1007-1016, Taylor & Francis, England (2010).

Kawasaki, H, et al. "Detection and evaluation of activation of various cancer antigenic peptide-specific CTLs in mature dendritic cells used for dendritic cell therapy," The 21st International Congress of Personalized Medicine, Conference Program and Abstracts, Personalized Medicine Universe (Japanese edition) 4(Supplement 2): 5 pages, Oct. 17, 2015.

Heldin, C.H., et al., "TGF-Beta Signalling from Cell Membrane to Nucleus through SMAD Proteins," Nature 390(6659):465-471, Nature Publishing Group, England (1997).

International Preliminary Report on Patentability for Application No. PCT/KR2014/004752, The International Bureau of WIPO, Switzerland, dated Nov. 1, 2016, 23 pages.

International Preliminary Report on Patentability for Application No. PCT/KR2015/003642, The International Bureau of WIPO, Switzerland, dated Oct. 12, 2016, 18 pages.

International Search Report for International Application No. PCT/KR2014/004752, Korean Intellectual Property Office, Republic of Korea, dated Jan. 16, 2015, 10 pages.

International Search Report for International Application No. PCT/KR2015/003642, Korean Intellectual Property Office, Republic of Korea, dated Jul. 3, 2015, 8 pages.

Massague, J., "Tgf-Beta Signal Transduction," Annual Review of Biochemistry 67:753-791, Annual Reviews, United States (1998).

Song, J., et al., "Characterization and. Fate of Telomerase-Expressing Epithelia during Kidney Repair," Journal of the American Society of Nephrology 22(12):2256-2265, American Society of Nephrology, United States (2011).

Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).

Written Opinion for International Application No. PCT/KR2014/004752, Korean Intellectual Property Office, Republic of Korea, dated Jan. 16, 2015, 21 pages.

Written Opinion for International Application No. PCT/KR2015/003642, Korean Intellectual Property Office, Republic of Korea, dated Jul. 3, 2015, 16 pages.

Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).

Zhang, H., et al., "Inhibiting TGFβ1 has a Protective Effect on Mouse Bone Marrow Suppression Following Ionizing Radiation Exposure in Vitro," Journal of Radiation Research 54(4):630-636 Oxford University Press, England (2013).

Co-pending U.S. Appl. No. 15/105,289, inventors Kim, Sang Jae, filed Jun. 16, 2016 (Not Yet Published).

Co-pending U.S. Appl. No. 15/303,370, inventors Kim, Sang Jae, filed Oct. 11, 2016 (Not Yet Published).

Co-pending U.S. Appl. No. 15/307,632, inventors Kim, Sang Jae, filed Oct. 28, 2016 (Not Yet Published).

Co-pending U.S. Appl. No. 15/346 870, inventors Kim, Sang Jae, filed Nov. 9, 2016 (Not Yet Published).

(56) References Cited

OTHER PUBLICATIONS

International Search Report for International Application No. PCT/KR2014/010035, Korean Intellectual Property Office, Republic of Korea, dated Feb. 2, 2015, 8 pages.
International Preliminary Report on Patentability for International Application No. PCT/KR2014/010035, Korean Intellectual Property Office, Republic of Korea, dated Apr. 26, 2016, 13 pages.
Written Opinion for International Application No. PCT/KR2014/010035, Korean Intellectual Property Office, Republic of Korea, dated Feb. 2, 2015, 11 pages.

* cited by examiner

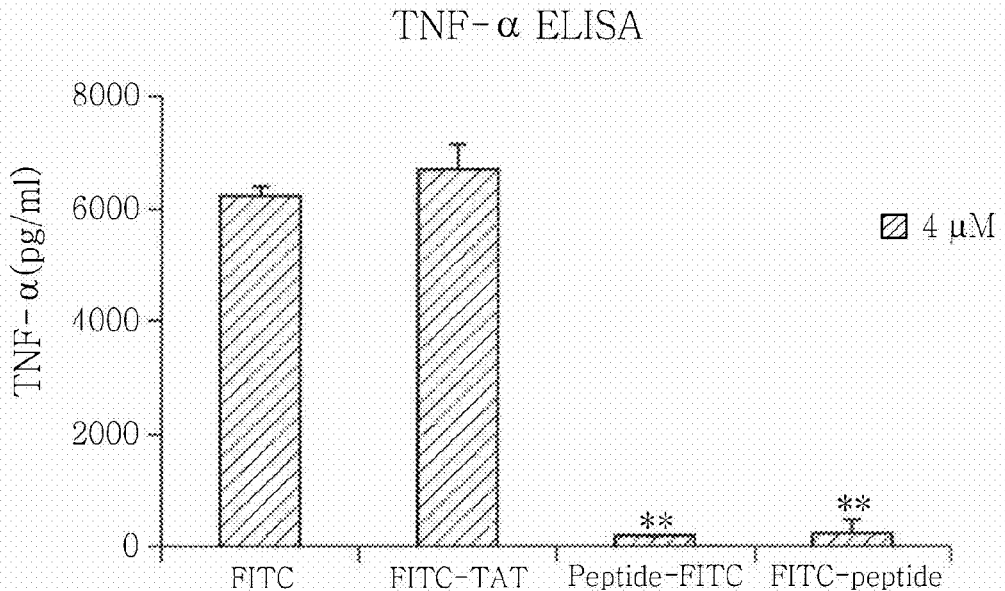
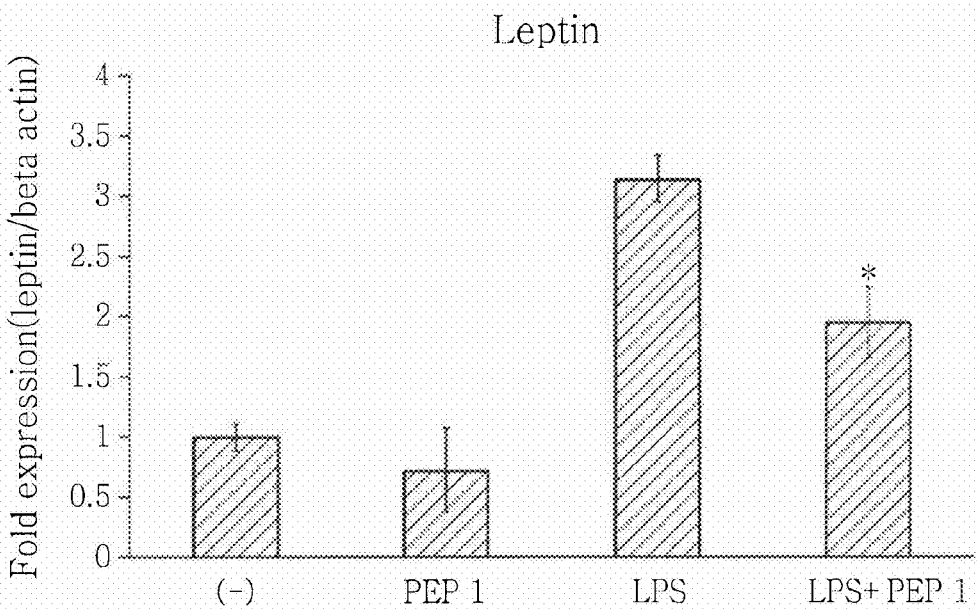

[Fig. 3]
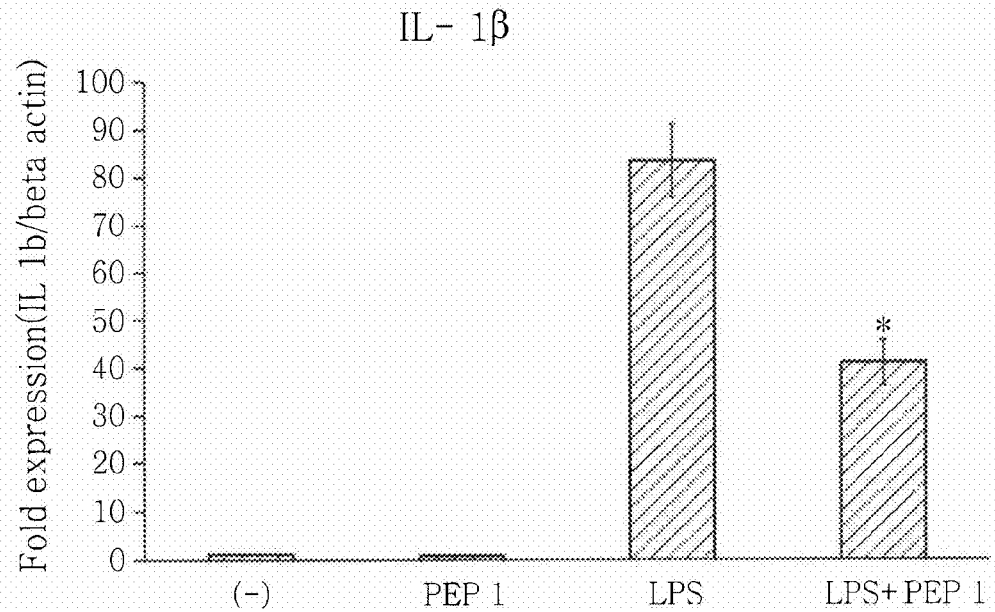
[Fig. 4]
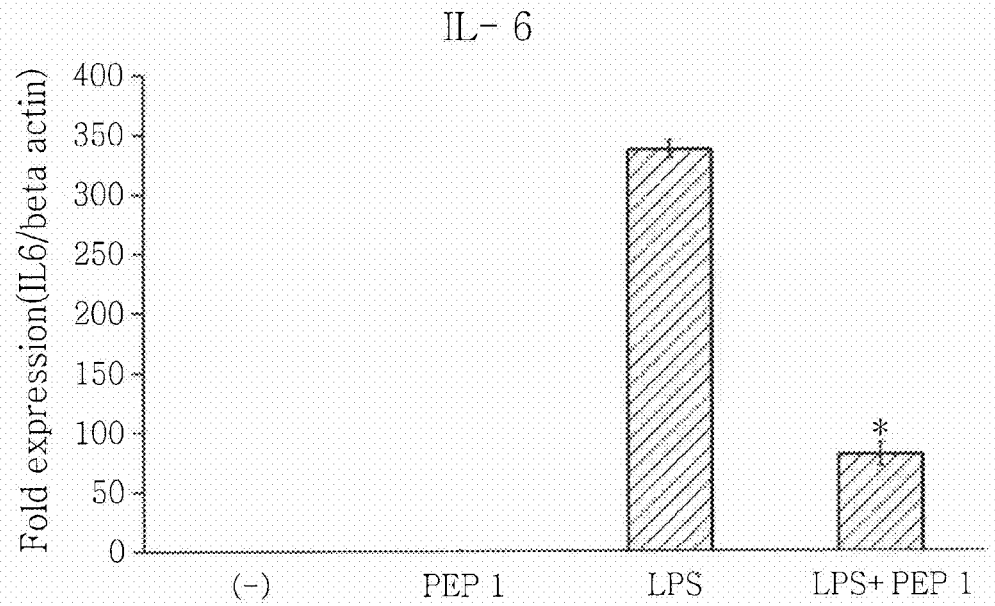

[Fig. 5]
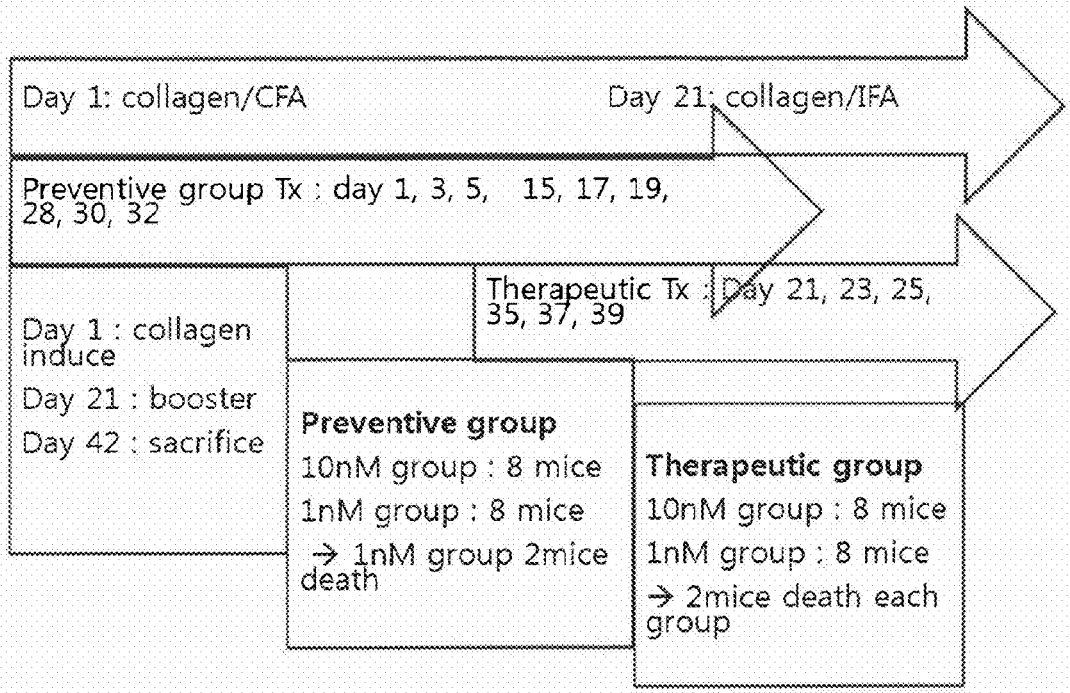
[Fig. 6]
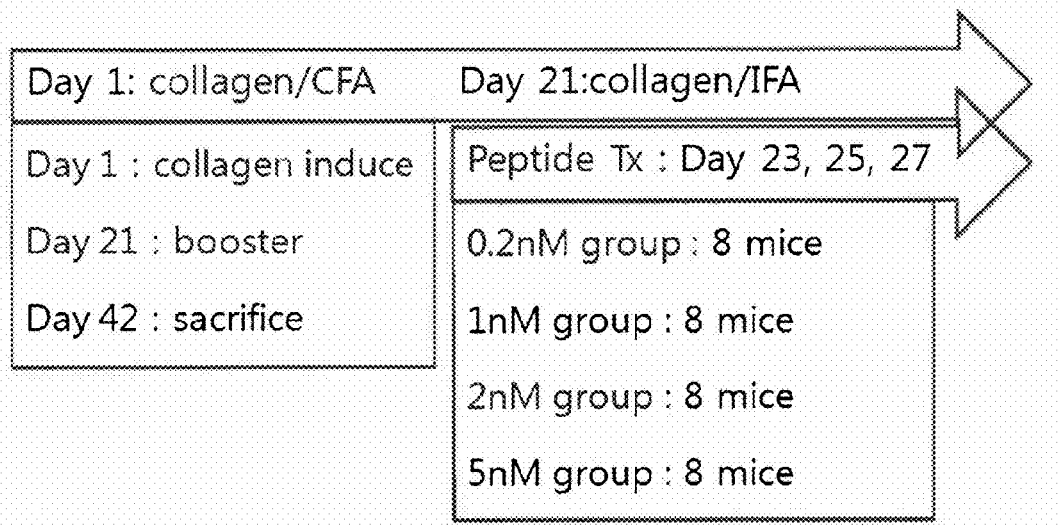

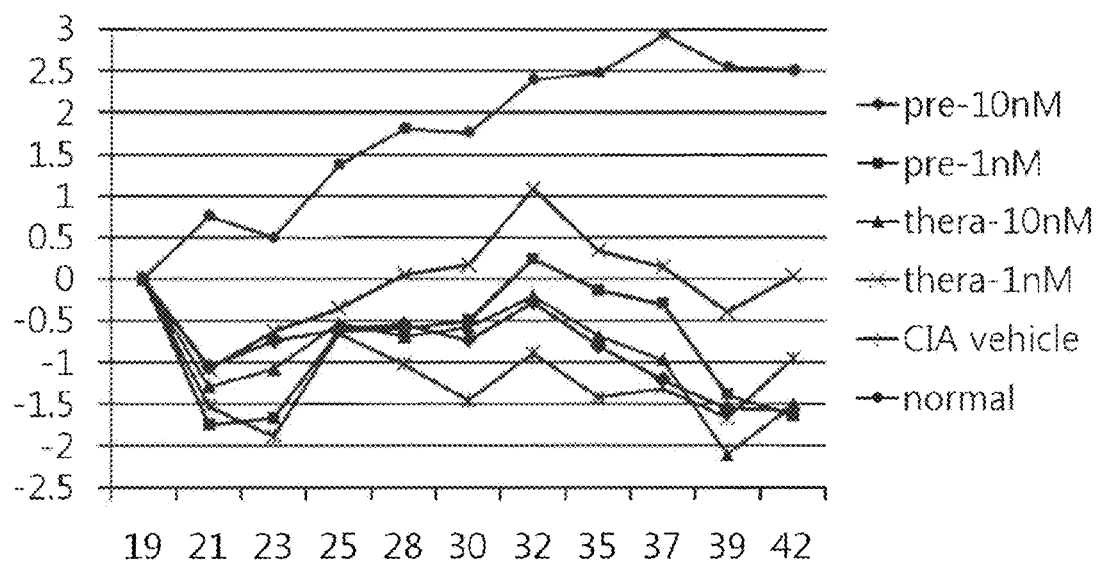
[Fig. 7]
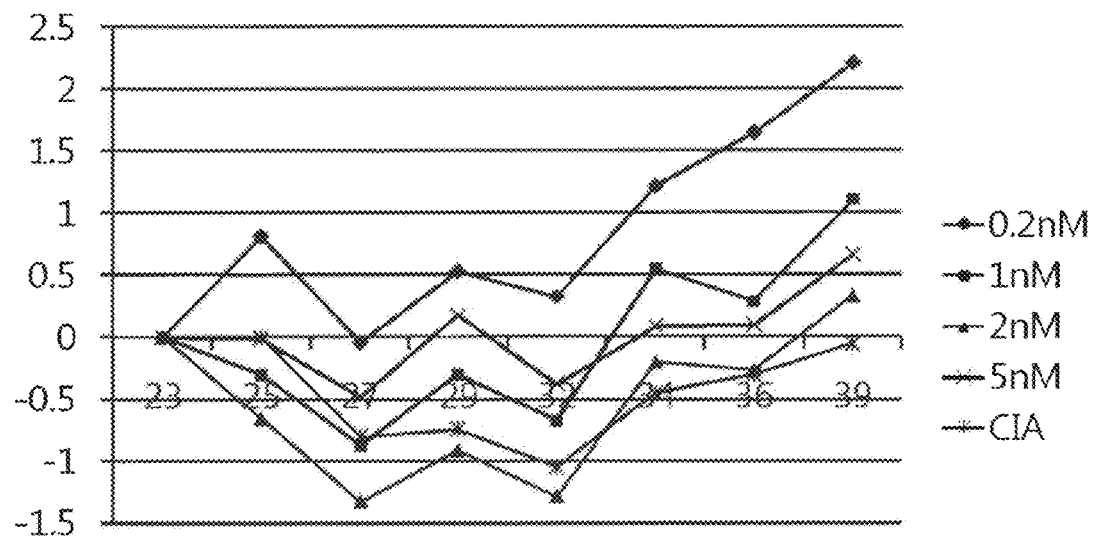
[Fig. 8]

[Fig. 9]
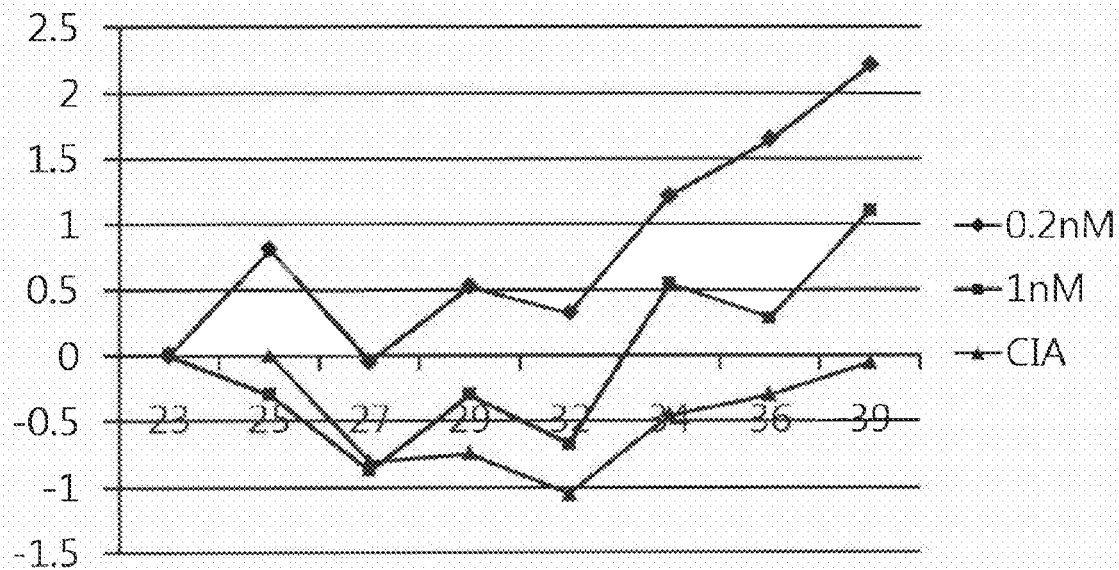
[Fig. 10]
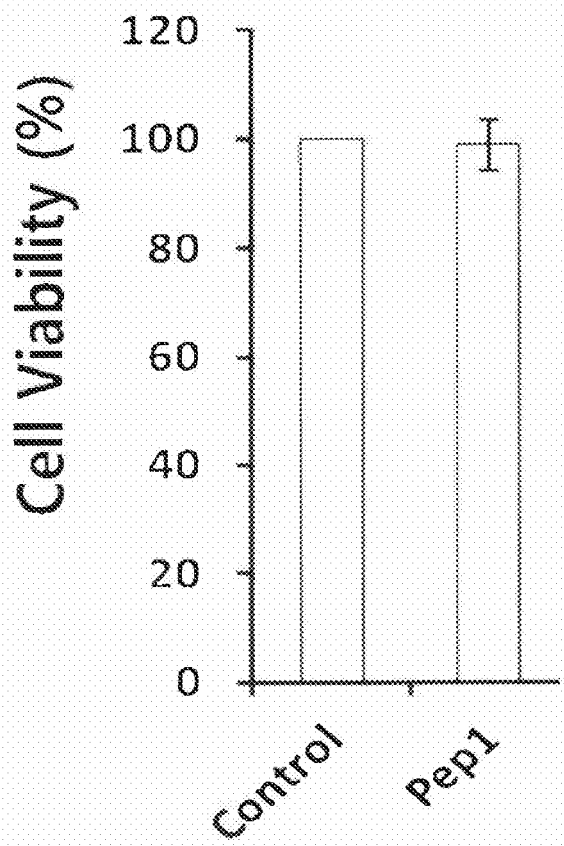

COMPOSITION FOR PREVENTING OR TREATING CACHEXIA

REFERENCE TO SEQUENCE LISTING SUBMITTED ELECTRONICALLY

The content of the electronically submitted sequence listing (Name 2473_0790004_Seq_Listing_Updated.txt; Size: 11,966 bytes; and Date of Creation: Aug. 19, 2015) filed with the application is incorporated herein by reference in its entirety.

BACKGROUND OF THE INVENTION

Technical Field

The present invention relates to a composition for preventing or treating cachexia, and more specifically, to a composition for preventing or treating cachexia containing a peptide derived from a telomerase.

Background Art

Cachexia is a syndrome that can be referred to the debility, a systemic disease which appears with multiple chronic disease, the most common symptoms are gradual weight loss, anemia, edema, and loss of the desire to eat.

The Major sign of cachexia is loss of adipose tissue as well as loss of muscle tissue and bone tissue. Accordingly, non-fat tissue is also known as "lean body mass". in addition, they appeared loss of the desire to eat (anorexia), weakness (asthenia), and decreased hemoglobin levels (anemia).

Cachexia is a complex metabolic syndrome represent only observed in these patients but, it appears to progressive weight loss of adipose tissue and skeletal muscle.

The treatment of cachexia is not just a matter of eating more. If the subject want to eat, if the subject trying to eat, even if administering nutrition to a subject through the stomach tube or intravenous, the state will not be convert to normal.

A recent studies on the cachexia found that the body response against the presence of cachexia under disease (Laviano A. et al., 2005).

Cachexia occurs caused by reduced nutritional intake and unbalanced of absorption and excretion by increased nutritional consumption of biological disease, the humoral factor derived from a lesion where is the part of the caused, have been described as including effects on the metabolism of the body. In order to improve of cachexia against the above problems it is required to intake of nutritional supplement, replacement for lack of energy and nutritional administrated for increase the immunity such as intravenous hyperalimentation.

As above the background of cachexia, it is required to develop therapeutic agent for the improving or suppressing the progress of cachexia.

BRIEF SUMMARY OF THE INVENTION

Disclosure

Technical Problem

The inventors of the present disclosure have made efforts to develop a composition effective in treating cachexia without harmful side effects and have completed the present disclosure.

The present disclosure is directed to providing a peptide effective in treating cachexia such as weight loss, anemia, edema, and loss of appetite comprising a peptide derived from a telomerase.

The present disclosure is directed to providing a composition effective in treating rheumatoid arthritis comprising a peptide derived from a telomerase.

Technical Solution

According to one embodiments of the present invention, provided is a composition for preventing or treating cachexia including a peptide that includes an amino acid sequence of SEQ ID No: 1, a peptide including an amino acid sequence having a sequence identity of 80% or greater to the amino acid sequence, or a peptide fragment of the above-mentioned peptides.

In a composition for preventing or treating cachexia according to an embodiment of the present invention, the peptide fragment includes three or more amino acids.

In a composition for preventing or treating cachexia according to an embodiment of the present invention, the peptide may be derived from human telomerase.

In a composition for preventing or treating cachexia according to an embodiment of the present invention, the composition may eliminate, prevent or treat symptoms related to cachexia in substance.

In a composition for preventing or treating cachexia according to an embodiment of the present invention, wherein the cachexia is caused by one or more selected from a group consisting of AIDS, cancer, after Hip Fracture, chronic heart failure, COLD (chronic obstructive pulmonary disease) and COPD (chronic obstructive pulmonary disease) comprising chronic obstructive pulmonary disease, Liver Cirrhosis, renal failure, rheumatoid arthritis comprising autoimmune disease, systemic lupus, sepsis, tuberculosis, cystic fibrosis, Crohn's disease and severe infections.

In a composition for preventing or treating cachexia according to an embodiment of the present invention, wherein the cachexia is caused by aging.

In a composition for preventing or treating cachexia according to an embodiment of the present invention, the composition may be provided in the solution concentration that is 5 nM/Kg or less.

In a composition for preventing or treating cachexia according to an embodiment of the present invention, the composition may be provided in the solution concentration more desirably that is from 0.15 nM/kg to 5 nM/kg.

In a composition for preventing or treating cachexia according to an embodiment of the present invention, the composition may be an external skin composition.

In a composition for preventing or treating cachexia according to an embodiment of the present invention, the composition may be a pharmaceutical composition.

In a composition for preventing or treating cachexia according to an embodiment of the present invention, the composition may be a food composition.

According to one embodiments of the present invention, provided is a method of preventing and treating cachexia, the method comprises the step of administering an effective amount of the composition for preventing or treating cachexia to a subject in need thereof.

In a method for preventing or treating cachexia according to an embodiment of the present invention, the composition may be provided in the solution concentration that is 5 nM/Kg or less.

In a method for preventing or treating cachexia according to an embodiment of the present invention, the composition may be provided in the solution concentration more desirably that is from 0.15 nM/kg to 5 nM/kg.

According to one embodiments of the present invention, provided is a use of the composition for preventing and treating cachexia.

In one embodiment, provided is a kit comprising a peptide comprising an amino acid sequence of SEQ ID No: 1, a peptide including an amino acid sequence having a sequence identity of 80% or greater to the amino acid sequence, or a peptide fragment of the above-mentioned peptides; and instructions at least one of administration dose, administration route, administration frequency, and indication of the peptide or composition.

Advantageous Effects

The composition for preventing or treating cachexia, according to the present invention, has the advantages of improving symptoms of cachexia, such as weight loss, anemia, edema, and loss of appetite, and has side effects.

BRIEF DESCRIPTION OF THE DRAWINGS/FIGURES

FIG. 1 is a graph which shows the results of performing TNF-α ELISA with the culture of monocytes derived from PBMC. The monocytes were stimulated with LPS (10 ng/ml) for two hours, then reacted with each peptide, FITC, FITC-TAT, PEP 1-FITC and FITC-peptide for two hours. (** P<0.01. Compared with the negative control (FITC and FITC-TAT).

FIG. 2 to FIG. 4 shows the effect of PEP 1 on the markers of cachexia such as Leptin, IL-1β, IL-6 confirmed by real time qPCR.

FIG. 5 and FIG. 6 shows schedules according to the time for the first and second experiments of inducing rheumatoid arthritis and treating peptides by using CIA animal models respectively.

FIG. 7 shows changes in body weight of a control group and a treatment group, wherein Y axis value indicates a body weight changes by using a unit of g. X axis value indicates treatment and time elapse.

FIG. 8 shows a result of the second experiment that presents changes of weight of a control group and 0.2 nM, 1 nM, 2 nM and 5 nM treatment groups, wherein Y axis value indicates a body weight changes by using a unit of g. X axis value indicates treatment and time elapse.

FIG. 9 is a graph illustrating the result of the treatment of peptides at low-concentrations(0.2 nM, 1 nM) which appears to be more effective result in FIG. 8, wherein Y axis value indicates a body weight changes by using a unit of g. X axis value indicates treatment and time elapse.

FIG. 10 shows the result of a toxicity test of Pep 1 in HeLa cells.

DETAILED DESCRIPTION OF THE INVENTION

Best Mode

Since the present invention can have adaptability for diverse transformation and examples of practical application, below is a more detailed description of the present invention. Nevertheless, this is no means to limit the form of practical application; it should be understood that the intention is to include the concept and the extent of technology in all of the transformation, equivalents to alternatives. In describing the present invention, if any detailed description about the prior art is considered to deteriorate the fundamental principles of the present invention, the description will be omitted.

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells.

A recent, Tumor Necrosis Factor (Tumor Necrosis Factor; TNF), monocytokine and cytokine which derived from macrophage may cause of cachexia. As above mentioned that TNF is probably the most common cause of cachexia due to produce inflammatory related cytokines. Therefore, it is directly observed in cancer patients and weight loss patients caused by severe infections. Hence, scientific research has been studied the various mechanism of TNF.

Thus, it was reported that Tumor Necrosis Factor (Tumor Necrosis Factor; TNF) called cachectin which is play a major role in cancer cachexia. The mechanism activity of cachectin is also same as cytokine such as interleukin (IL), IL-6, LIF and IFN (KR 2001-0012613 A).

In addition, J. Walsmith et al., 2002 reported that weight loss occurred is not caused by anorexia alone, chronic inflammation is also lead to weight loss. Furthermore, another study found that weight loss occurred in adjuvant induced arthritis in mouse, as well as they seem to be loss of muscle mass and muscle fiber. This research showed the express of gene such as TNF-α (Tumor Necrosis Factor-α) and IL-1β (interleukin-1β) can be induced in the skeletal muscle. Importantly, the expression of TNF-α and IL-1β in the skeletal muscle lead to a negative correlation with skeletal muscle fiber.

Hence, in the prior arts, showed that the prevent for loss of skeletal muscle mass more effectively in adjuvant induced arthritis in mouse by blocking both of TNF-α and IL-1 at the same time rather than only blocked TNF-α. The combination of TNF-α and IL-1β leads to muscle wasting. Therefore, TNF-α not only affected to cachexia but, IL-1β can be presented evidence for occurs cachexia.

Cachexia occurs in chronic disease caused by loss of adipose tissues and the desire to eat, which is a unique disease with characteristics that lead to reduced body mass due to the loss of non-fat mass. Anorexia nervosa causes the cachexia can be observed in cancer, CHF, COPD, CKD and the aging. This can be related with inflammatory factors such as TNF-α, IL-6, IL-2, and IL-1β. Those inflammatory markers are able to regulate the feedback mechanism of hypothalamus, also it is contribute to the progress of cachexia.

Also, Leptin is a hormone which acts as secreted by adipose tissue, reduced the food consumption by acting on the hypothalamus, stimulated energy consumption leads to weight loss. Cachexia caused by CKD (Chronic kidney disease)- and CHF (congestive heart failure) which indicated the high levels of leptin (Diana R. Engineer et al., 2012). In R. Roubenoff et al., 1997, the chronic inflammatory represented in the rheumatoid arthritis (RA) which is related with loss of body cell mass. These symptoms are called as inflammatory cachexia which represented with hypermetabolism and degradation of protein in rheumatoid arthritis without malabsorption.

In other words, according to the experiment, it is presumed that adjuvant arthritis leads to weight loss and joint swell. Also, this study found that reduced cell mass leads to weight loss and was higher than the rate of weight loss. As a result, weight loss caused by inflammatory which directly closed to the reduced consumption of food intake and increased the production of TNF-α and IL-1 in splenocytes (R. Roubenoff et al., 1997). Also, the research of Michael J. Tisdale, 2009 found that muscle atrophy which represented in cachexia, its blocked by IL-6 receptor antibody in overexpression interleukin-6 in IL-6 transgenic mice.

According to this study, severe symptoms of cachexia and polyps are represented in mouse, which exhibited high amounts of IL-6 but, ApcMin+/IL6-/- mouse is not exhibiting any loss and low amounts of polyps. Also, overexpression interleukin-6 in transgenic mice showed the loss of skeletal muscle and polyps formed, but conversely, cannot find any loss of skeletal muscle in mouse without tumors.

Also, this research provided that muscle protein degradation by increased IL-6 which leads to activated the decomposed pathway of non-lisosome (for example, proteasome) protein and lisosome (cathepsin) protein (Michael J. Tisdale, 2009).

Cachexia is a weakness syndrome which can be referred to various disease such as AIDS, cancer, after Hip Fracture, chronic heart failure, COLD (chronic obstructive pulmonary disease) and COPD (chronic obstructive pulmonary disease) comprising chronic obstructive pulmonary disease, Liver Cirrhosis, renal failure, rheumatoid arthritis comprising autoimmune disease, systemic lupus, sepsis, tuberculosis, cystic fibrosis, Crohn's disease and severe infections. as well as weakness observed in aging.

In an exemplary embodiment of the present disclosure, a peptide of SEQ ID NO 1, a peptide which is a fragment of the peptide of SEQ ID NO 1 or a peptide having 80% or more sequence identity with the peptides includes a peptide derived from telomerase, specifically human (*Homo sapiens*) telomerase.

The peptides disclosed herein may include peptides comprising an amino acid sequence at least 80%, at least 85%, at least 90%, at least 95%, at least 96%, at least 97%, at least 98%, at least 99% of sequence homology with the peptide of SEQ ID NO 1 or a fragment thereof. Moreover, the peptides disclosed in the present invention may include peptides having differences from SEQ ID NO: 1 or a fragment thereof in at least one amino acids, at least 2 amino acids, at least 3 amino acids, at least 4 amino acids, at least 5 transformed amino acids, at least 6 transformed amino acids, or at least 7 amino acids.

In one embodiment of the present invention, changes in amino acids include modifications of peptide's physical and chemical characteristics. For example, amino acid modification can be performed for improving thermal stability of the peptide, altering substrate specificity, and changing the optimal pH.

The term "amino acid" herein includes not only the 22 standard amino acids that are naturally integrated into a peptide but also the D-isomers and modified amino acids. Therefore, in a specific embodiment of the present invention, a peptide herein includes a peptide having D-amino acids. On the other hand, a peptide may include non-standard amino acids such as those that have been post-translationally modified. Examples of post-translational modification include phosphorylation, glycosylation, acylation (including acetylation, myristorylation, plamitoylation), alkylation, carboxylation, hydroxylation, glycation, biotinylation, ubiquitinylation, modification in chemical properties (e.g. β-removing deimidation, deamidation) and structural modification (e.g. formation of disulfide bridge). Also, changes of amino acids include the changes of amino acids that occur due to chemical reaction during the combination process with cross-linkers for formation of a peptide conjugate, such as changes in an amino group, carboxyl group or side chain.

A peptide disclosed herein may be a wild-type peptide that has been identified and isolated from natural sources. On the other hand, when compared to SEQ ID NO: 1 or its fragments, the peptides disclosed herein may be artificial variants that comprise one or more amino acids substituted, deleted and/or inserted. Amino acid alteration in wild-type polypeptides—not only in artificial variants—comprises protein folding and/or conservative substitutions of amino acids that do not influence activities significantly. Examples of conservative substitutions may be within the groups of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activities are known in the art. Most common occurring alterations are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations thereof. Other examples of conservative substitutions are shown in the following table 1.

TABLE 1

| Original amino acid | Examples of residue substitution | Preferable residue substitution |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | ala | Ala |
| Ser (S) | thr | Thr |
| Thr (T) | ser | Ser |
| Trp (W) | tyr; phe | Tyr |
| Tyr (Y) | trp; phe; thr; ser | Phe |
| Val (V) | ile; leu; met; phe; ala; norleucine | Leu |

The substantial modification of the biological properties of peptides are performed by selecting significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in a target area, or (c) the efficacy of maintaining the bulk of the side chain. Natural residues are divided into groups by general side chain properties as the following:

(1) hydrophobicity: Norleucine, met, ala, val, leu, ile;
(2) neutral hydrophilicity: cys, ser, thr;
(3) acidity: asp, glu;
(4) basicity: asn, gln, his, lys arg;
(5) residue that affects chain orientation: gly, pro; and
(6) aromaticity: trp, tyr, phe.

Non-conservative substitutions may be performed by exchanging a member of the above classes with that of different classes. Any cysteine residues that are not related to maintaining the proper three-dimensional structure of the peptide can typically be substituted with serine, thus increasing the oxidative stability of the molecule and preventing improper cross-linkage. Conversely, improvement of stability can be achieved by adding cysteine bond(s) to the peptide.

Another type of amino acid variants of peptides are those having a changed pattern of peptide glycosylation. The term "change" herein means deletion of at least one carbohydrate residues that are found in a peptide and/or addition of at least one glycosylated residues that do not exist within a peptide.

Glycosylation in peptides are typically N-linked or O-linked. The term "N-linked" herein refers to that carbohydrate residues are attached to the side chain of asparagine residues. As tripeptide sequences, asparagine-X-serine and asparagine-X-threonine (wherein the X is any amino acid except proline) are a recognition sequence for attaching a carbohydrate residue enzymatically to the side chain of asparagine. Therefore, with the presence of one of these tripeptide sequences in a polypeptide, the potential glycosylation sites are created. "O-linked glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of glycosylation site to a peptide is conveniently performed by changing an amino acid sequence to contain the tripeptide sequence mentioned above (for N-linked glycosylation sites). These changes may be made by addition of at least one serine or threonine residues to the first peptide sequence, or by substitution with those residues (for O-linked glycosylation sites).

The SEQ ID No: 1 (hereinafter 'PEP 1') as used herein is a telomerase-derived peptide comprised of 16 amino acids.

```
                                                SEQ ID NO: 1
EARPALLTSRLRFIPK
```

Also, in one aspect, the present invention is a peptide comprising amino acid sequence of SEQ ID NO: 1, a peptide having above 80% homology of amino acid sequence with above-mentioned sequence, or a fragment of the above-mentioned peptides has an advantage in that it has high feasibility due to its low toxicity within a cell.

In one aspect, the present invention is a composition for preventing or treating cachexia comprising, as an active ingredient, a peptide comprising amino acid sequence of SEQ ID NO: 1, a peptide having above 80% homology with above-mentioned sequence, or a fragment of the above-mentioned peptides.

In one aspect, the present invention is a method for preventing or treating cachexia comprising administration of a peptide comprising amino acid sequence of SEQ ID NO: 1, a peptide having above 80% homology with above-mentioned sequence, or a fragment of the above-mentioned peptides to a subject in need thereof.

In one aspect, the present invention is a use of a peptide for preventing or treating cachexia comprising administration of a peptide comprising amino acid sequence of SEQ ID NO: 1, a peptide having above 80% homology with above-mentioned sequence, or a fragment of the above-mentioned peptides to a subject in need thereof.

In one aspect, the present invention is a kit comprising a peptide comprising an amino acid sequence of SEQ ID No: 1, a peptide including an amino acid sequence having a sequence identity of 80% or greater to the amino acid sequence, or a peptide fragment of the above-mentioned peptides; and instructions at least one of administration dose, administration route, administration frequency, and indication of the peptide or composition.

In one aspect, the fragment may consist of at least 3 amino acids. In other aspects, the fragment may consist of at least 4 amino acids, at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, or at least 15 amino acids.

In one aspect, the peptide may be derived from human telomerase. Specifically, the peptide of SEQ ID NO:1 means the peptide position in 611-626 of an entire human telomerase sequence (1132 amino acids, SEQ ID NO:2).

In one aspect, the peptide may be used for eliminating symptoms related to carchexia, or preventing or treating cachexia.

In one aspect, the peptide may be administered in a single dose of from 0.001 to 1 ng/kg or from 0.01 to 0.4 ng/kg. In other aspect, the dose of administering may be at least 0.001 ng/kg, at least 0.005 ng/kg, at least 0.01 ng/kg, at least 0.02 ng/kg or at least 0.03 ng/kg.

In other aspect, the dose of administering may be less than 1 ng/kg, less than 0.9 ng/kg, less than 0.8 ng/kg, less than 0.7 ng/kg, less than 0.6 ng/kg, less than 0.5 ng/kg, less than 0.4 ng/kg, less than 0.3 ng/kg, less than 0.2 ng/kg.

In one aspect, the peptide may be administered in once at 1-5 days or in once at 1.5-2.5 days.

In one aspect, the composition may contain a peptide of 0.05-5 nM concentrations.

In one aspect, the composition may be formulated for injection.

According to an embodiment of the present invention, the composition may contain 0.1 μg/mg to 1 mg/mg, specifically 1 μg/mg to 0.5 mg/mg, more specifically 10 μg/mg to 0.1 mg/mg of a peptide comprising an amino acid sequence of SEQ ID NO: 1, a peptide comprising an amino acid sequence having a sequence identity of 80% or greater to the amino acid sequence, or a peptide fragment thereof. When the peptide is contained in the above-mentioned range, all the safety and stability of the composition may be satisfied and cost-effectiveness may be achieved.

According to an embodiment of the present invention, the composition may have applications to all animals including humans, dogs, chickens, pigs, cows, sheep, guinea pigs, and monkeys.

According to an embodiment of the present invention, a pharmaceutical composition may be administered through oral, rectal, transdermal, intravenous, intramuscular, intraperitoneal, intramedullary, epidural, or subcutaneous means.

Forms of oral administration may be, but not limited to, tablets, pills, soft or hard capsules, granules, powders, solutions, or emulsions. Forms of non-oral administration may be, but not limited to, injections, drips, lotions, ointments, gels, creams, suspensions, emulsions, suppositories, patches, or sprays.

According to an embodiment of the present invention, the pharmaceutical composition, if necessary, may contain additives, such as diluents, excipients, lubricants, binders, disintegrants, buffers, dispersants, surfactants, coloring agents, aromatics, or sweeteners. According to an embodiment of the present invention, the pharmaceutical composition may be manufactured by conventional methods of the industry in the art.

According to an embodiment of the present invention, the active ingredient of the pharmaceutical composition may vary according to the patient's age, sex, weight, pathology state and severity, administration route, or prescriber's judgment. Dosage may be determined by one of ordinary skill in the art based on the above-mentioned factors, and the daily dose may be, but is not limited to, about 0.0000001 ng/kg/day to about 10000 ng/kg/day or about 0.00001 ng/kg/day to about 100 ng/kg/day, specifically about 0.0001 ng/kg/day to about 10 ng/kg/day, and more specifically about 0.01 ng/kg/day to about 0.4 ng/kg/day. According to an embodiment of the present invention, the pharmaceutical composition may be administered, but is not limited to, 1 to 3 times per 1 to 5 days.

The terms used herein is intended to be used to describe the embodiments, not to limit the present invention. Terms without numbers in front are not to limit the quantity but to show that there may be more than one thing of the term used. The terms "comprising", "having", "including" and "containing" shall be interpreted openly (i.e. "including but not limited to").

Mention of a numerical range is used instead of stating separate numbers within the range, so unless it is explicitly stated, the range should be construed as if all the numbers within the range are separately described herein. The end values of all the ranges are included in the range and can be combined independently.

Unless otherwise noted or clearly contradicting in context, all methods mentioned herein can be performed in a proper order. The use of any one embodiment and all embodiment, or exemplary language (e.g., "such as", "like ~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meanings ordinarily understood by a person skilled in the art that the present invention belongs to.

The preferred embodiments of the present invention include the best mode known to the inventors to perform the present invention. Variations in the preferred embodiments can become clear to those skilled in the art after reading the statements above. The present inventors hope that those skilled in the art can use the variations adequately and present invention be conducted in other ways than listed herein. Thus, the present invention, as allowed by the patent law, includes equivalents, modifications and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

Mode For Invention

Hereinafter, the present disclosure will be described in detail through examples and test examples. However, the following examples and test examples are for illustrative purposes only and it will be apparent to those of ordinary skill in the art that the scope of the present disclosure is not limited by the examples and test examples.

EXAMPLES

Example 1

Synthesis of Peptide

The peptide of SEQ ID NO: 1 was synthesized according to the conventionally known method of solid phase peptide synthesis. More specifically, the peptide was synthesized by coupling each amino acid from C-terminus through Fmoc solid phase peptide synthesis, SPPS, using ASP48S (Peptron, Inc., Daejeon Republic of Korea). Those peptides with their first amino acid at the C-terminus being attached to a resin were used as follows:

$NH_2$-Lys(Boc)-2-chloro-Trityl Resin
$NH_2$-Ala-2-chloro-Trityl Resin
$NH_2$-Arg(Pbf)-2-chloro-Trityl Resin All the amino acids to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in an acid. Examples include the followings:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetamethylaminium hexafluorophosphate]/ HOBt [N-Hydroxybenzotriazole]/NMM [4-Methylmorpholine] were used as the coupling reagents. Piperidine in 20% DMF was used to remove Fmoc. In order to remove the protection from residues or to separate the synthesized peptides from Resin, cleavage cocktail [TFA (trifluoroacetic acid)/TIS (triisopropylsilane)/ EDT (ethanedithiol)/ $H_2O$=92.5/2.5/2.5/2.5] was used.

The peptide synthesis was performed by using solid phase scaffold with the repetition of the following processes: starting with the amino acid protection, separate reaction of each amino acid, washing with solvents, and deprotection. Each peptide was synthesized by using the solid phase scaffold combined to starting amino acid with the amino acid protection, reacting the corresponding amino acids separately, washing with a solvent and deprotected, and repeating the processes. Upon the release from the resin, the synthesized peptides were purified by HPLC, validated by Mass Spectrometry, and freeze-dried, and verified for synthesis by MS, and then freeze-dried.

Specific peptide synthesis process is described as the following based on the synthesis process of PEP 1 which has SEQ ID: NO. 1.

1) Coupling

The amino acid (8 equivalent) protected with $NH_2$-Lys(Boc)-2-chloro-Trityl Resin, and coupling agent HBTU (8 equivalent)/HOBt (8 equivalent.)/NMM (16 equivalent) melted in DMF were mixed together, and incubated at room temperature (RT) for 2 hr. Following the incubation, the reaction mixture was subjected to the sequential washes of DMF, MeOH, and DMF.

2) Fmoc deprotection

Piperidine in 20% DMF was added and incubated at RT for 5 minutes 2 times, then sequentially washed with DMF, MeOH, and DMF.

3) Making the basic framework of peptide, NH$_2$-E(OtBu)-A-R(Pbf)-P-A-L-L-T(tBu)-S(tBu)-R(Pbf)L-R(Pbf)-F-I-P-K(Boc)-2-chloro-Trityl Resin) by repeating the above-mentioned reactions 1) and 2).

4) Cleavage: Cleavage Cocktail was added to the completely synthesized peptide, thus separating the synthesized peptide from the resin.

5) Pre-chilled diethyl ether was added into the obtained mixture, and then centrifugation was used to precipitate gathered peptide.

6) After purification by Prep-HPLC, the molecular weight was confirmed by LC/MS and lyophilized to produce in a powder form.

PEP 1 prepared by the method described in Example 1 was used to perform an experiment of effectiveness to preventing or treating rheumatoid arthritis.

Example 2

Investigation of the Inhibitory Effect of Pep1 on TNF-α Level in HepG2 Cells

Experiment 3-1: Cell Culture

PBMC (peripheral blood mononuclear cell) was separated from the blood samples (50 ml) collected from healthy subjects using Ficoll-Paque™ PLUS (GE Healthcare Life Sciences, Piscataway, N.J., USA). PBMCs were then enriched in complete RPMI 1640 medium containing 20% of human serum, followed by transferring to 100 mm polystyrene cell culture plate coated with human serum for 30 mins. After 2 hr incubation at 37° C. and 5% CO$_2$, the monocytes were detached from the bottom of cell culture plate using cold PBS (Phosphate Buffered Saline) (Gibco/Life Technologies, Carlsbad, Calif., USA), and 1×10$^5$ cells were cultured in each well of 96-well plate in RPMI 1640 medium (supplemented with penicillin-streptomycin; 100 mg/ml, human serum; 20%) overnight.

For Luciferase Analysis, HEK293/null (human embryonic kidney) cells and HEK293/TRL stably expressing TLR2 (toll-like receptor2) obtained from Seoul National University School of Dental Medicine were used. One day before the luciferase experiment, 2.5×10$^5$ cells were seeded into each well of 12-well plate and cultured overnight in DMEM (Dulbecco's modified Eagle's medium) medium (supplemented with blasticidin; 10 μg/ml, fetal bovine serum; 10%)(Invitrogen/Life Technologies, Carlsbad, Calif., USA)

Analysis of TNF-α(Cytokine Assay)

To investigate the effect of PEP-1 on TNF-α level in terms of protein expression level, ELISA (enzyme linked immunosorbent assay) was performed. 1×10$^5$ PBMC-derived monocytes were cultured in 96-well plate overnight. After then, LPS (lipopolysaccharide; 10 ng/ml, Sigma) was treated for 2 hours, followed by 3 times washes with PBS. OPTI-MEM medium (Invitrogen/Life Technologies, Carlsbad, Calif., USA) was then treated for an hour to induce the starvation, and 4 uM of FITC (Fluorescein Isothiocyanate), FITC-TAT, PEP-1-FITC, and FITC-PEP-1 were treated for 2 hours before measuring the TNF-α level. After culturing, cell soup was collected, and the amount of TNF-α was measured using ELISA kit (R&D, Minneapolis, Minn., USA) as follows.

TNF measurement uses sandwich ELISA method. 100 μl of TNF-α primary antibody was added into each well of pre-coated 96-well plate, and the plate was incubated at 4° C. overnight. On next day, the plate was washed 3 times with 0.5% Tween20 wash solution for 5 min each, and then 100 μl of each sample and standard solution was added and left at room temperature for 2 hrs. After washing the plate like above, 100 μl of HRP-conjugated secondary antibody was added into each well and left at room temperature for 2 hrs. Again, plate was washed, and avidin/biotin was added for measuring the absorbance. TNF-α level of each sample was quantified using the standard graph calculated from the absorbance of standard solution.

PBMC-derived monocytes were stimulated with endotoxin LPS (10 ng/ml) for 2 hrs, starved for 1 hr using OPTI-MEM, and then 4 uM of FITC, FITC-TAT, PEP 1-FITC and FITC-PEP 1 were treated for 2 hrs. After incubation, TNF-α level was measured with cell culture medium using ELISA. As a result, in case of FITC and FITC-TAT, TNF-α level increased due to LPS (6.2 and 6.7 ng/ml, respectively), but TNF-α level significantly decreased in case of PEP-1-FITC and FITC-PEP-1 (0.17 and 0.25 ng/ml, respectively) and the difference was statistically significant ($P<0.01$) (FIG. 1).

Example 3

Analysis of Peptides Effect on Cachexia Marker Leptin, IL-1β and IL-6 in THP1 Cell Line THP1 Cell culture THP-1 cell culture was performed to investigate the effects of PEP 1 on cachexia markers. THP-1 (Human acute monocytic leukemia derived cell line) cell was purchased from ATCC (American Type Culture Collection, Manassas, Va., USA), cell was maintained in RPMI-1640 (Life technologies, Carlsbad, Calif., USA) supplemented with 10% FBS (Life technologies), 1% penicillin/streptomycin and 2-mercaptoethanol (Sigma-Aldrich, St. Louis, Mo., USA), and cells were cultured in a 37° C., 5% CO$_2$ humidified incubator.

In general, THP-1 cells were grown under suspension condition, and it was differentiated into adherent macrophages by treating cells with phorbol myristate acetate (PMA) for 24 hr. THP-1 cells (3×10$^6$ cells/plate, 95~confluency) were seeded into well plate for incubator.

PEP 1 Treatment

After differentiation of THP-1 cells, macrophage-like THP-1 cells were washed two times using complete RPMI 1640 (5 min/wash). Then, cells were treated with 10 ng/ml LPS and/or 20 μM PEP 1 at 37° C. for 4 hr.

Isolated RNA and Synthesized cDNA in THP1 Cell Line

Total RNA samples were isolated from peptide-treated THP-1 cells by using Trizol (QIAzol) reagent and, and cDNA was synthesized by reverse transcriptase PCR using reverse transcription PCR kit from Promega following manufacturer's protocol.

Real Time qPCR

Then, cDNA samples were used as a template for synthesized by real time qPCR. Real time PCR primers for leptin, IL-1β and IL-6 shown in Table 2. real time qPCR was performed using CFX96 (Bio-Rad) instrument with SYBR Green system. The PCR cycling conditions were 95° C. for 10 min for activation of HotStart DNA Taq Polymerase, followed by 50 cycles of 95° C. for 10 sec, 55° C. for 30 sec, and 72° C. for 30 sec. All samples were measured in triplicate and differences in gene expression were calculated using the 2-cycle threshold method. All the data were normalized against β actin (housekeeping gene) and presented as means of +/−S.E. from at least three independent experiments.

TABLE 2

Primer for Human leptin, IL-1β and IL-6

| Gene | Forward primer | Reverse primer |
|---|---|---|
| beta actin | AGAAAATCTGGCACCACACC | GGGGTGTTGAAGGTCTCAAA |
| leptin | TGCCTTCCAGAAACGTGATCC | CTCTGTGGAGTAGCCTGAAGC |
| IL1β | GGACAAGCTGAGGAAGATGC | TCGTTATCCCATGAGTCGAA |
| 1L6 | CCTGAACCTTCCAAAGATGGC | TTCACCAGGCAAGTCTCCTCA |

The result of the above experiment, THP-1 cells are involved in the inflammatory responses induced by LPS then the levels of leptin, IL-1β and IL-6 were decreased in THP-1 cells after being treated with PEP 1 (see FIG. 2 to FIG. 4).

Example 4

Cachexia Treatment Effect of Peptide in Rheumatoid Arthritis Mouse Model

Establishing CIA (Collagen Induced Arthritis) Animal Model

In order to find effectiveness of the peptide according to the present invention to rheumatoid arthritis (RA), CIA (collagen induced arthritis) mouse were used to confirmation.

Non-patent document disclosed in the present invention describes about CIA animal model in detail. In reference to this, the present embodiment established the CIA animal model as follows.

In the first and second experiment mentioned below, lyophilized and formed in powder PEP1 according to the Example 1 was dissolved in 0.9% saline solution and was used. After doing amendment of the purity (purity: 97.3%, content: 85.3%) of PEP1, the solution for injection was made in each concentration with 0.9% saline solution as an additive just before an administration. Every dose was administered by the solution in an amount of 100 µl.

The First Experiment

The first induction was done to 38 mice at day 1 by using 5-weeks male DBA/1J mouse (Orient Bio Inc., Korea), and the mice were divided into the preventive group consisting of 16 mice administered by a peptide composition before CIA inducement (i.e. 8 mice of 1 nM, 100 µl (around 0.2 ng dose) and 8 mice of 10 nM, 100 µl (around 2 ng dose)), the therapeutic group consisting of 16 mice administered by a peptide composition after CIA inducement (i.e. 8 mice of 1 nM, 100 µl and 8 mice of 10 nM, 100 µl), and the PBS treatment group consisting of 6 mice.

To the preventive group, the treatment was done by intradermal injection in each suitable concentration at day 2, 4, 6, 21, 23, 25, 35, 37 and 39. At day 19, the second inducement was done to 38 mice, and to the therapeutic group the treatment by intradermal injection in each suitable concentration at day 21, 23, 25, 35, 37 and 30 from day 21 (see FIG. 1).

The assessment of rheumatoid arthritis index was done at from the day of second inducement to the day 42 per every two days and the joint and serum was collected after sacrificing all mice at day 42.

During the administration of PEP1 all mice were survived.

The Second Experiment

Like the first experiment, the first inducement was done to 38 mice at day 1 by using 5-week mice, the mice were divided into the group consisting of 32 mice administered by a peptide composition before CIA inducement (8 mice of 0.2 nM, 100 µl (i.e. around 0.04 ng); 8 mice of 1 nM, 100 µl (around 0.2 ng dose); 8 mice of 2 nM, 100 µl (i.e. around 0.4 ng); 8 mice of 5 nM, 100 µl (i.e. around 1 ng)) and the PBS treatment group consisting of 6 mice.

The second inducement was done at day 21, and the treatment was done by intradermal injection in each suitable concentration to each group at day 23, 25 and 27 (see FIG. 2).

The assessment of rheumatoid arthritis index was done at from the day of second inducement to the day 42 per every two days and the joint and serum was collected after sacrificing all mice at day 42.

During the administration of PEP1 all mice were survived.

Result of the First Experiment

The preventive group (pre-1 nM and pre-10 nM) showed the decreasing arthritis effect until day 36 and after then the decreasing effect has gone. The therapeutic group (thera-1 nM and thera-10 nM) showed the decreasing arthritis effect in whole period but the 10 nM group showed the more effect than the 1 nM group. Also, the preventive group and the therapeutic group showed increased body weights compared to the CIA control group (see FIG. 5 to FIG. 7).

Result of the Second Experiment

When the peptide treatment group of each concentration compared with the CIA control group, the peptide treatment group appeared to decrease the arthritis index in whole period. Also, when the body weights were measured, the increased body weight was confirmed at the low-level peptide treatment group compared to CIA control group (see FIG. 9).

As summarizing the result of the first and second experiments mentioned above, the administration of 1 nM peptide was more effective than the 1 nM peptide having lower level, and the therapeutic group treated after second inducement was more effective to inhibit rheumatoid arthritis than the preventive group. Also, as a result of measuring the change of the body weight in each group, decrease of body weight in the therapeutic group of the 1 nM peptide treatment is lower than any other group and this is also the effect of inhibiting arthritis.

Example 5

Toxicity Test

Cell Culture

HeLa cell line was purchased from ATCC. The HeLa cell line was maintained in MEM supplemented with 10% fetal bovine serum (Invitrogen, USA), Earle's salts, non-essential amino acids, sodium pyruvate, 100 ug/ml penicillin and 100 units/ml streptomycin, and then incubated at 37° C., 5% $CO_2$.

Cell Viability and Toxicity Analysis

The cells were seeded into 96-well plates and added to each well for medium supplemented with 10% fetal bovine serum (Invitrogen, USA), 100 ug/ml penicillin and 100 units/ml streptomycin. The cells were cultured in 37° C., 5%

$CO_2$ for 12 h incubator. After incubated, plates washed by PBS, and added MEM (Minimum essential medium) for starvation during 1 h. The 20 uM of PEP 1 with 100 μl of the aqueous solution were added to each well, and then the cells were incubated at 37° C. for 24. After incubated, the cell viability and toxicity were evaluated using an MTT assay. The result are shown in FIG. 10.

PRIOR ART

Patents

KR 2001-0012613 A

Non-Patents

Choi, Sang Gyu, "Recent Advances in Cancer Cachexia", J. Korean Oncol. Nurs., 1, 20-25 (2011)

Kern et al., Cancer Cathexia, J. Parenteral and Enteral Nutrition, 12, 286-298 (1988)

American Journal of Medicine, 85, 289-291 (1988)

Laviano A. et al., Nat. Clin. Pract. Oncol. 2:158-65 (2005)

J. Walsmith et al., "Cachexia in rheumatoid arthritis", International Journal of Cardiology, Vol. 85, Issue 1, pp. 89-99, 2002

Diana R. Engineer and Jose M. Garcia, "Leptin in Anorexia and Cachexia Syndrome", International of Peptides, Vol. 2012, Article ID 287457, 13 pages, 2012

R. Roubenoff et al., "Adjuvant arthritis as a model of inflammatory cachexia", Arthritis and Rheumatism, Vol. 40, No. 3, pp. 534-539, 1997

Michael J. Tisdale, "Mechanisms of Cancer Cachexia", Physiological Reviews, Vo. 89, No. 2, pp. 381-410, 2009

Kim et al., "Experimental Animal Models for Rheumatoid Arthritis: Methods and Applications", Journal of Rheumatic Disease, Vol. 19, No. 4, August 2012

What is claimed is:

1. A method for treating cachexia caused by rheumatoid arthritis comprising administering to a subject in need thereof the isolated peptide of SEQ ID NO: 1.

2. The method according to claim 1, wherein the peptide is administered in a single dose at a concentration of 0.001 to 1 ng/kg.

3. The method according to claim 1, wherein the peptide is administered in a single dose at a concentration of 0.01 to 0.4 ng/kg.

4. The method according to claim 1, wherein the peptide is administered 1 to 3 times a day.

5. The method of claim 1, wherein the peptide is administered at a daily dose of 0.001 to 1 ng/kg.

6. The method of claim 5, wherein the peptide is administered 1 to 3 times daily.

7. A method for treating cachexia caused by rheumatoid arthritis comprising administering to a subject in need thereof a composition comprising the isolated peptide of SEQ ID NO: 1.

8. The method of claim 7, wherein the composition is administered through oral, rectal, transdermal, intravenous, intramuscular, intraperitoneal, intramedullary, epidural, or subcutaneous routes.

9. The method of claim 7, wherein the composition comprises 0.1 µg/mg to 1 mg/mg of isolated peptide.

10. The method of claim 7, wherein the peptide is administered in a single dose at a concentration of 0.001 to 1 ng/kg.

11. The method of claim 7, wherein the peptide is administered in a single dose at a concentration of 0.01 to 0.4 ng/kg.

12. The method of claim 7, wherein the peptide is administered 1 to 3 times a day.

13. The method of claim 12, wherein the peptide is administered at a daily dose of 0.001 to 1 ng/kg.

14. The method of claim 13, wherein the peptide is administered 1 to 3 times daily.

15. The method of claim 7, wherein the composition is a pharmaceutical composition.

16. The method of claim 15, wherein the composition is formulated for injection.

* * * * *

SEQUENCE LISTING

```
<160> NUMBER OF SEQ ID NOS: 10

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
            85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
            165                 170                 175

Gln Leu Gly Ala Ala Thr Gln Ala Arg Pro Pro Pro His Ala Ser Gly
            180                 185                 190
```

```
Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Ala Thr Ser Leu Glu Gly Ala
        275                 280                 285

Leu Ser Gly Thr Arg His Ser His Pro Ser Val Gly Arg Gln His His
        290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
        370                 375                 380

Arg Tyr Trp Gln Met Arg Pro Leu Phe Leu Glu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605
```

-continued

His Arg Glu Ala Arg Pro Ala Leu Leu Thr Ser Arg Leu Arg Phe Ile
610             615                 620

Pro Lys Pro Asp Gly Leu Arg Pro Ile Val Asn Met Asp Tyr Val Val
625             630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Gly Leu Asp Asp Ile His Arg
                675                 680                 685

Ala Trp Arg Thr Phe Val Leu Arg Val Arg Ala Gln Asp Pro Pro
690                 695                 700

Glu Leu Tyr Phe Val Lys Val Asp Val Thr Gly Ala Tyr Asp Thr Ile
705             710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
            850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
            1010                1015                1020

Gln Val Trp Lys Asn Pro Thr Phe Phe Leu Arg Val Ile Ser Asp

```
        1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 3
<211> LENGTH: 20
<212> TYPE: DNA
<213> ORGANISM: Artificial Sequence
<220> FEATURE:
<223> OTHER INFORMATION: beta actin forward primer

<400> SEQUENCE: 3
agaaaatctg gcaccacacc                                              20

<210> SEQ ID NO 4
<211> LENGTH: 20
<212> TYPE: DNA
<213> ORGANISM: Artificial Sequence
<220> FEATURE:
<223> OTHER INFORMATION: beta actin reverse primer

<400> SEQUENCE: 4
ggggtgttga aggtctcaaa                                              20

<210> SEQ ID NO 5
<211> LENGTH: 21
<212> TYPE: DNA
<213> ORGANISM: Artificial Sequence
<220> FEATURE:
<223> OTHER INFORMATION: leptin forward primer

<400> SEQUENCE: 5
tgccttccag aaacgtgatc c                                            21

<210> SEQ ID NO 6
<211> LENGTH: 21
<212> TYPE: DNA
<213> ORGANISM: Artificial Sequence
<220> FEATURE:
<223> OTHER INFORMATION: leptin reverse primer

<400> SEQUENCE: 6
ctctgtggag tagcctgaag c                                            21

<210> SEQ ID NO 7
<211> LENGTH: 20
<212> TYPE: DNA
<213> ORGANISM: Artificial Sequence
<220> FEATURE:
<223> OTHER INFORMATION: IL1 beta forward primer
```

```
<400> SEQUENCE: 7
ggacaagctg aggaagatgc                                                    20

<210> SEQ ID NO 8
<211> LENGTH: 20
<212> TYPE: DNA
<213> ORGANISM: Artificial Sequence
<220> FEATURE:
<223> OTHER INFORMATION: IL1 beta reverse primer

<400> SEQUENCE: 8
tcgttatccc atgagtcgaa                                                    20

<210> SEQ ID NO 9
<211> LENGTH: 21
<212> TYPE: DNA
<213> ORGANISM: Artificial Sequence
<220> FEATURE:
<223> OTHER INFORMATION: IL6 forward primer

<400> SEQUENCE: 9
cctgaacctt ccaaagatgg c                                                  21

<210> SEQ ID NO 10
<211> LENGTH: 21
<212> TYPE: DNA
<213> ORGANISM: Artificial Sequence
<220> FEATURE:
<223> OTHER INFORMATION: IL6 reverse primer

<400> SEQUENCE: 10
ttcaccaggc aagtctcctc a                                                  21
```